US00PP08415P

United States Patent [19]

Zaiger et al.

[11] Patent Number: Plant 8,415

[45] Date of Patent: Oct. 12, 1993

[54] PEACH TREE "SNOW KING"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 999,202

[22] Filed: Dec. 31, 1992

[51] Int. Cl.[5] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach tree, its novelty consists of the following unique combination of features that are outstanding in a new variety.

1. Heavy and regular bearer of fruit.
2. Having large, firm, white flesh, freestone fruit.
3. Fruit with excellent flavor and eating quality.
4. The ability of the fruit to stay firm on the tree 6–7 days after maturity (shipping ripe).
5. Fruit with a high degree of attractive red skin color.
6. Vigorous upright growth.

1 Drawing Sheet

ORIGIN OF THE VARIETY

The present new variety of peach tree was developed by us in our experimental orchard located near Modesto, Calif. as a first generation cross between two selections with the field identification numbers 33R320 and 29G672. The female parent 33R320 originated from a cross between a nectarine of unknown parentage and Redwing Peach (U.S. Plant Pat. No. 621). The pollen parent 29G672 originated from seed of an open pollinated O'Henry Peach (U.S. Plant Pat. No. 2,964). We grew and maintained a large group of these first generation seedlings under careful observation, during which time the present variety exhibited the distinctive desirable fruit characteristics described above and was selected for asexual reproduction and commercialization.

ASEXUAL REPRODUCTION OF THE VARIETY

The new and distinct variety of peach tree was asexually propagated by budding, as performed by us in our experimental orchard located near Modesto, Calif. and shows that all characteristics are established and transmitted through succeeding propagations and come true to the original tree in all respects.

SUMMARY OF THE VARIETY

The herein described variety of peach tree is of large size, vigorous upright growth and a productive and regular bearer of large, firm, white flesh, freestone fruit with excellent flavor and eating quality. The fruit is relatively uniform in ripening throughout the tree, holds firm on the tree 6 to 7 days after maturity (shipping ripe), has good handling and shipping quality and ripens in the late maturity season, approximately 5 to 6 days after O'Henry Peach (U.S. Plant Pat. No. 2,964).

DESCRIPTION OF THE PHOTOGRAPHS

The accompanying photographic illustrations show typical specimens of the foliage and fruit of the present new variety of peach tree, with the upper and lower surface of the leaves being illustrated, an exterior and sectional view of the fruit being divided in the suture plane to reveal flesh coloration, pit cavity and a stone remaining in place. The photographic illustrations were taken shortly after being picked at maturity (shipping ripe) and the colors are as nearly true as reasonably possible in a color representation of this type.

DESCRIPTION OF THE VARIETY

The botanical details of this new and distinct variety of peach tree, its flowers, foliage and fruit are based on observations of specimens grown in our experimental orchard, located near Modesto, Calif. with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.

Trunk:
- *Size.*—Large.
- *Texture.*—Medium shaggy.
- *Color.*—Brown to dark brown (5-F-6) to (5-F-8).

Branches:
- *Size.*—Medium.
- *Texture.*—Medium rough.
- *Lenticels.*—Numerous. Large size.
- *Color.*—Light brown to dull brown.

Leaves:
- *Size.*—Large. Average length — 6⅝". Average width — 1½".
- *Form.*—Lanceolate — pointed.
- *Texture.*—Smooth.
- *Margin.*—Crenate.
- *Petiole.*—Size — Medium. Average length — ½". Medium thickness.
- *Glands.*—Number varies from 1 to 4. Average number 2. Reniform. Located on lower portion of leaf blade and upper portion of petiole.

Flower buds:
- *Size.*—Medium to large.
- *Form.*—Plump.
- *Pubescence.*—Pubescent.

Flowers:
- *Size.*—Large — showy.

*Blooming period.*—Mar. 3, 1991 to Mar. 9, 1991. Varies slightly with climatic conditions.

*Pollen.*—Present.

*Color.*—Pink.

Fruit:

*Maturity when described.*—Firm ripe.

*Date of first picking.*—Aug. 5, 1991.

*Date of last picking.*—Aug. 9, 1991.

*Size.*—Large. Comparatively uniform. Average diameter axially 3¼" to 3¾". Average transversely in suture plane 3¼" to 3¾".

*Form.*—Nearly Globose — slightly flattened at stem end.

*Suture.*—Shallow. Extends from base to apex.

*Ventral surface.*—Usually rounded, some fruit very slightly lipped.

*Cavity.*—Rounded to slightly elongated in suture plane. Average depth — ⅝". Average breadth — 1".

*Base.*—Retuse.

*Apex.*—Usually slight pistil point. Varies from slight pistil point to rounded.

Flesh:

*Color.*—White to pinkish white (8-A-1) to (8-A-2). Stone cavity — red to geranium red (11-A-7) to (11-B-8) extending into flesh, heavier near apex.

*Texture.*—Firm.

*Ripens.*—Evenly.

*Juice.*—Moderate.

*Flavor.*—Excellent, mild, sweet, subacid.

*Eating quality.*—Excellent.

*Fibers.*—Few, tender.

*Amygdalin.*—Undetected.

*Aroma.*—Moderate.

Skin:

*Thickness.*—Medium.

*Texture.*—Medium tough — tenacious to flesh.

*Tendency to crack.*—None.

*Down.*—Moderate. Medium length.

*Color.*—White to pinkish white ground color (9-A-1) to (9-A-2). Nearly overspread with red to deep red (11-B-7) to (11-C-8).

Stone:

*Type.*—Freestone.

*Size.*—Medium to large. Average length — 1⅜" to 1½". Average breadth — 1" to 1⅛". Average thickness — ½ to ⅝".

*Form.*—Oval to Ovoid.

*Base.*—Usually straight, varies from straight to rounded.

*Apex.*—Cuspidate.

*Sides.*—Equal to unequal.

*Surface.*—Irregularly furrow toward apex, pitted toward base.

*Ridges.*—Usually rounded.

*Tendency to split.*—Very slight.

*Color.*—Brown to reddish brown (10-E-7) to (10-F-7).

Use:

*Market.*—Local and long distance. Dessert.

Keeping quality: Good.

Shipping quality: Good.

The new variety of peach tree, its flowers, foliage and fruit may vary in slight detail due to climatic, soil conditions and cultural practices under which the variety may be grown, the present botanical description is that of the variety produced and grown under the ecological conditions prevailing near Modesto, Calif.

We claim:

1. A new and distinct variety of peach tree, substantially as illustrated and described, characterized by its large size, vigorous upright growth and a productive and regular bearer of large, white flesh, freestone fruit with excellent flavor and eating quality; the fruit is further characterized by having firm flesh with good handling and shipping quality, holding firm on the tree 6 to 7 days after maturity (shipping ripe), having an attractive red skin color and ripening in the late maturity season, approximately 5 to 6 days after O'Henry Peach (U.S. Plant Pat. No. 2,964).

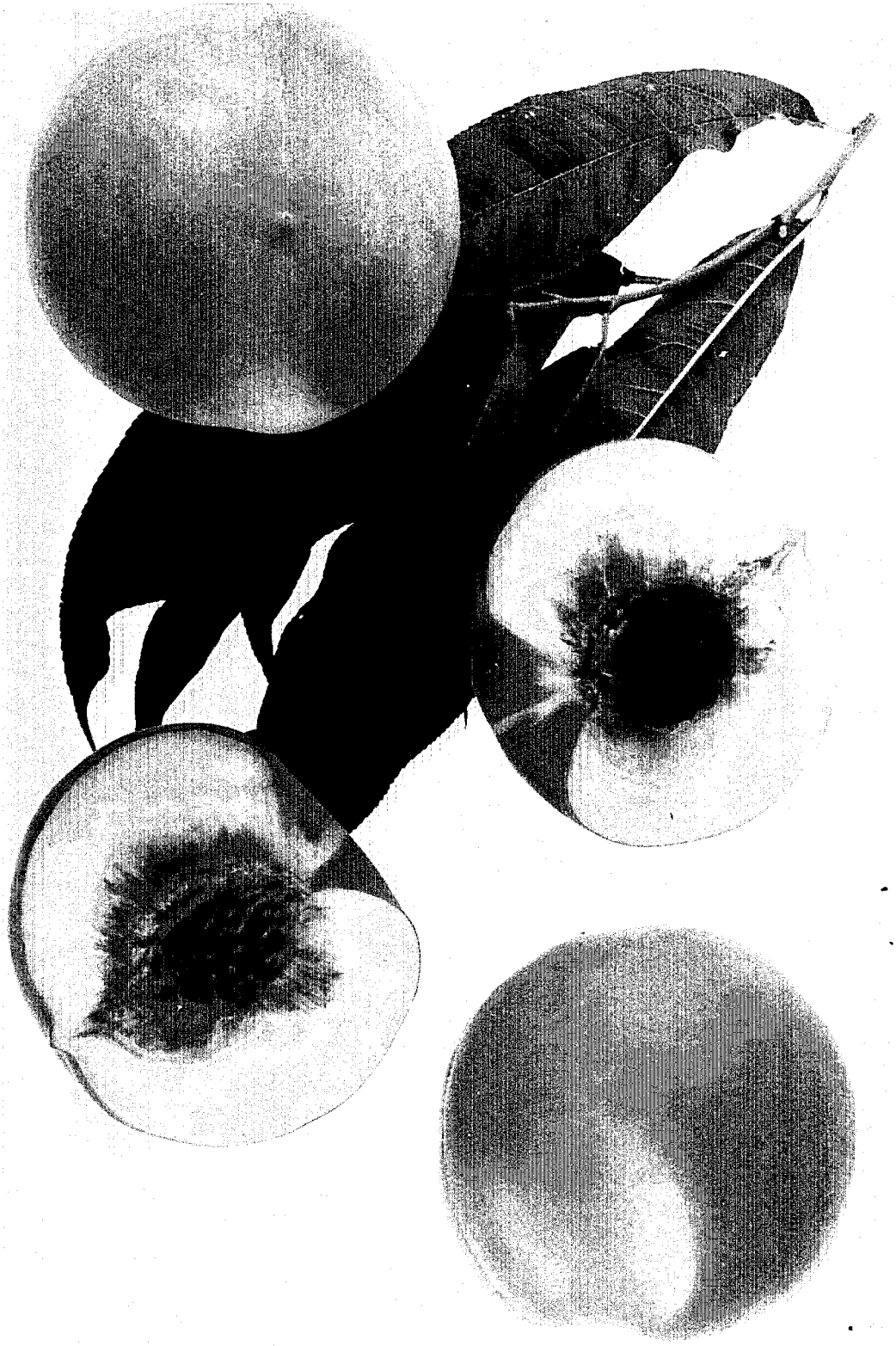

* * * * *